United States Patent [19]

Kennedy et al.

[11] Patent Number: 5,163,991
[45] Date of Patent: Nov. 17, 1992

[54] BIOCONTROL OF JOINTED GOATGRASS

[75] Inventors: Ann C. Kennedy; Alex G. Ogg, Jr.; Frank L. Young, all of Pullman, Wash.

[73] Assignee: The United States of America as represented by the Secretary of Agriculture, Washington, D.C.

[21] Appl. No.: 597,150

[22] Filed: Oct. 15, 1990

[51] Int. Cl.$^5$ .................... A01N 63/00; C12N 1/20
[52] U.S. Cl. .................... 71/79; 435/253.3
[58] Field of Search .................... 71/79

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,390,360 | 6/1983 | Walker | 71/79 |
| 4,419,120 | 12/1983 | Walker | 71/79 |
| 5,030,562 | 7/1991 | Elliott et al. | 435/29 |

OTHER PUBLICATIONS

Hoagland, R. E. *Microbes and Microbial Products as Herbicides*, Chapter 1, pp. 2-11,, Am. Chem. Soc. Nat'l Metting, Apr. 1989.

Donald; William W. et al., "Biology and Control of Jointed Goatgrass (*Aegilops cylindrica*), a Review", Weed Technology, vol. 5: pp. 3-17 (1984).

Kimber, Gordon et al., "Wild Wheat An Introduction", Special Report 353 College of Agriculture, University of Missouri Columbia, pp. 1-43, (Apr. 1987).

Bowden; Wray M., "The Taxonomy and Nomenclature of the Wheats, Barleys, and Ryes and Their Wild Relatives", Canadian Journal of Botany, vol. 37: pp. 657-684, (1959).

*Primary Examiner*—Richard L. Raymond
*Assistant Examiner*—S. Mark Clardy
*Attorney, Agent, or Firm*—M. Howard Silverstein; John D. Fado; Margaret A. Connor

[57] ABSTRACT

A method for screening bacteria to select strains which inhibit the weed jointed goatgrass in small grain crops under field conditions and methods for field application of the bacteria to inhibit jointed goatgrass in small grain crops in a commercial setting are described. Strains useful for biocontrol of jointed goatgrass are disclosed.

14 Claims, No Drawings

BIOCONTROL OF JOINTED GOATGRASS

BACKGROUND OF THE INVENTION

1. Field of the Invention

The invention relates to the isolation, selection, and application of novel strains of bacteria which have the ability to control the weed jointed goatgrass in small grain crops without deleteriously affecting the crop.

2. Description of the Art

Jointed goatgrass (*Aegilops cylindrica*) is a winter annual grass that is a major weed species in the winter wheat producing areas of the western United States. Over 3 million acres of winter wheat in the western U.S. are infested with this weed, reducing yields by about 15-20%. There is no selective herbicide available for the control of jointed goatgrass in a grass crop, e.g., a small grain crop. This is because jointed goatgrass and winter wheat are genetically similar (they share the same D genome). Further, the life cycles of jointed goatgrass and winter wheat and winter barley are very similar. Another problem is that jointed goatgrass seed is viable in the soil for at least four years. At the present time, producers must grow spring crops continuously for a minimum of three years to reduce the jointed goatgrass seed reservoir in the soil to a manageable level. This cultural control method has a serious economic disadvantage because the yield of spring wheat is about 40% lower than winter wheat.

Use of antagonistic microorganisms for biological control of some weeds have been reported. However, no bacterial strain has been previously found which would control the weed jointed goatgrass; additionally, no procedure for the selection of bacteria which inhibit jointed goatgrass in small grain crops has been reported. Because the physiological characteristics required for a bacterial strain to control weeds are very specific as to (1) the weed to be controlled; (2) the mode of action of weed control; (3) the activity and ecological niche of the microorganism; and (4) cultural practices and soil and climatic conditions favorable for control, information about microorganism treatments for control of weeds other than jointed goatgrass cannot be used to predict strains of microorganisms which would reduce jointed goatgrass under field conditions or predict criteria for selecting such strains.

SUMMARY OF THE INVENTION

We have discovered a novel method for screening bacteria for selection of those strains which will inhibit (reduce the incidence or severity of) the growth of the weed jointed goatgrass in small grain crops under field conditions and a practical and effective method for application of the inhibitory bacteria to suppress jointed goatgrass growth in the field.

The bacterial strains selected by our method inhibit the growth of jointed goatgrass in small grain crops such as wheat, barley, and related crops without deleteriously affecting the crops. The selected strains have the ability to inhibit jointed goatgrass in the field without deleteriously affecting the small grain crop when used as a treatment on the crop area to be protected or used as a small grain crop seed treatment. Such treatments include spraying the field with an inhibitory amount of the selected bacteria, applying an inhibitory amount to the subsurface of the soil, e.g., furrow, or applying bacteria to or with the crop seed in an amount sufficient to inhibit jointed goatgrass when the crop seed is planted in the field.

The need for a biological control of jointed goatgrass in cropland has long been recognized as crop losses due to this weed have been significant and no selective chemical herbicide is available. By using the procedures and conditions of our screening method, strains of bacteria can be selected which will inhibit jointed goatgrass growth in the field. By using our application method, jointed goatgrass growth can be controlled in a commercial setting.

In accordance with this discovery, it is an object of the invention to provide a means for screening bacteria to select those strains which inhibit jointed goatgrass in small grain crops under field conditions without deleteriously affecting the small grain crop to be protected.

It is also an object of the invention to provide a method for biologically controlling jointed goatgrass in small grain crops under field conditions using the strains selected by our method.

Another object of the invention is the provision of a method to identify root colonizing bacteria that inhibit jointed goatgrass and utilize the strong root colonizing ability of the organisms to establish on the roots of jointed goatgrass in the field. Similar to other bacterial strains, it is difficult to take these organisms from the growth chamber to the field due to variables such as soil conditions, soil moisture, temperature, and the like. By the use of our method, however, it is possible to assess bacteria for field effectiveness and to apply jointed goatgrass-inhibitory bacteria for control of jointed goatgrass in small grain crops.

Another object of the invention is the provision of novel strains of bateria which inhibit jointed goatgrass in field grown wheat without deleteriously affecting the wheat.

Other objects and advantages of the invention will become apparent from the ensuing description.

DEPOSIT OF BIOLOGICAL MATERIAL

Bacterial isolates 47-5, 47-7, and 3361 described herein (Examples 2-4) have been identified as Pseudomonas species and have been deposited in the Agricultural Research Culture Collection (NRRL) in Peoria, IL, and have been assigned Accession Nos. NRRL B-18776, NRRL B-18777 and NRRL 18778, respectively. The original deposit at NRRL was made on Feb. 28, 1991, and was converted to a deposit under the Budapest Treaty on Mar. 18, 1991.

DESCRIPTION OF THE PREFERRED EMBODIMENTS

The screening method comprises:

Step 1: Isolation of Strains of Potentially Inhibitory Bacteria

To biologically control jointed goatgrass, a bacterial strain must have the ability to establish and grow in the microhabitat where it is to be used to inhibit the growth of the weed. This means it must have the ability to colonize the root system of jointed goatgrass. Such bacteria are selected by isolating strains from the rhizoplane (root surface) or rhizosphere (soil immediately surrounding the roots) or both rhizoplane and rhizosphere of (a) jointed goatgrass plants or (b) small grain crops. Although strains from the rhizoplane or rhizosphere of one small grain may be isolated in this step for potential use to control another small grain crop, it is preferred that the bacterial strain be isolated from the variety of small grain to be protected as it is likely to best function in the ultimate biocontrol habitat.

Winter wheat is the small grain crop which is most significantly affected by jointed goatgrass by reduction in crop yield and resultant economic loss. For the purposes of description of our method, winter wheat is used as exemplary of the crop to be protected, however, our method is applicable to other small grain crops, for example, winter barley, spring wheat, spring barley, and related crops.

The isolation procedure is as follows: winter wheat plants or jointed goatgrass plants are dug from the field and adhering soil gently washed from the roots with flowing tapwater. The roots are excised from the tops. The bacteria are collected and isolated by standard procedures. For example, bacteria can be isolated by placing the excised roots in sterile dilution blanks containing sterile water and glass beads and shaking the mixture vigorously to remove organisms clinging to the root surface. Then serial dilutions are prepared and spread plated on to a selective medium such as King's Medium B supplemented with novobiocin, penicillin, and cycloheximide (KMB NPC) (Sands and Rovira, *Applied Microbiology* 20:513-514 (1970)), and incubated at a suitable temperature, e.g., 20° C. For short term storage during the screening procedure, inoculum from individual colonies is placed on a KMB NPC slant.

Step 2: Screening of the Bacterial Strains In Vitro

Bacterial strains isolated in step 1 are screened to select those strains which inhibit jointed goatgrass growth in vitro as exhibited by reduction in root growth or germination as compared to control plants. Those strains which are inhibitory to jointed goatgrass are then tested against wheat; those strains which do not deleteriously affect wheat growth in vitro are selected.

In the in vitro screening procedure, individual colonies are inoculated into a medium suitable for growing up the colonies, for example, Pseudomonas minimal salts medium (PMS) described by Gasson, *Applied and Environmental Microbiology* 39: 25-29 (1980), and grown at at a suitable temperature, e.g., about 20° C. until late logarithmic growth (about $10^9$ to $10^{11}$ cells per ml culture medium). The cells are then treated in at least one of the following ways: (1) the culture is used directly, (2) the culture is centrifuged to obtain a substantially cell-free culture supernatant (not more than about $10^4$ cells per ml of supernatant), or (3) the cell culture is centrifuged and filter sterilized to obtain a cell-free culture filtrate (no cells present). The first method assays both the effect of the organism and the effect of toxin production by the organism on jointed goatgrass growth. The second method is a quick assay to determine the effect of toxin production by the organism on the growth of jointed goatgrass. The third method assays only the effect of toxin production by the organism on jointed goatgrass growth. The assay method using the culture filtrate is preferred.

Jointed goatgrass growth inhibition is assessed by adding to petri plates a standard quantity, usually 2 ml, of the cell culture, substantially cell-free culture supernatant, or cell-free culture filtrate. A standard quantity, usually 18 ml, of 0.9% molten agar (50° C.) is added to each plate, the contents mixed, and allowed to solidify. Generally two plates are prepared for each organism tested. Control plates are prepared by using PMS instead of the cell culture, substantially cell-free culture supernatant, or cell-free culture filtrate. The plates are planted with dehusked jointed goatgrass seeds, 10 seeds per plate is convenient, and allowed to grow at a suitable temperature, e.g., 15° C. The plates are slanted slightly so the roots grow down and across the plate. Before root growth from the seedlings interferes with each other, about 5 days, the seedlings are pulled from the agar and root length or germination or both are recorded. The organisms showing significant inhibition of jointed goatgrass growth (length) or germination when compared to the control are tested against winter wheat seedling growth. For the purposes of this invention, significant inhibition of jointed goatgrass in the in vitro test is defined as at least a 50% reduction in root growth (length) when compared to the control or at least a 20% reduction in germination when compared to the control.

The strain selected above is assessed against wheat as follows: Test tubes receive a standard quantity, usually 1 ml each, of the cell culture, substantially cell-free culture supernatant, or the cell-free culture filtrate which was used in the jointed goatgrass test, and a standard quantity of 0.9% molten agar (50° C.), usually about 9 ml, is added to each tube, the contents mixed, and the tube slanted. Generally 10 growth tubes are prepared for each organism tested. Control tubes are prepared identically except that PMS is substituted for the cell culture, substantially cell-free culture supernatant, or the cell-free culture filtrate. When solidified, pregerminated winter wheat seeds (one per tube) are planted mid-slope on the slants and allowed to grow at a suitable temperature, e.g., 15° C. Before root growth reaches the bottom of the tube, approximately 3-6 days, the seedlings are pulled from the growth tubes and root length recorded. A bacterial strain is denoted as one that does not deleteriously affect winter wheat when root growth reduction of the bacterial treated wheat is less than 25% when compared to the control wheat seedlings.

Pure cultures of the strains significantly inhibiting jointed goatgrass growth with little or no effect on winter wheat growth are individually streaked onto a suitable medium such as KMB NPC and selected and restreaked until the strain is pure and stable. Each individual strain is grown up and maintained so as to keep it stable such as by storing in glycerol at $-10°$ C. or lyophilizing and storing at $-10°$ C.

Step 3: Screening of the Bacterial Strains in the Growth Chamber

Bacterial strains isolated in the step 2 are subjected to a first screening in soil by separately growing jointed goatgrass plants and wheat plants in a growth chamber or greenhouse in the presence of the bacterial strain selected in step 2. In this step, those strains are selected which, at a particular concentration, inhibit jointed goatgrass without deleteriously affecting wheat.

In this test, pots are filled with soil and seeded with jointed goatgrass or with wheat seeds. We have found that 6.4 cm diameter by 7.6 cm deep plastic pots seeded with 6-10 dehusked jointed goatgrass seeds and 7.6 cm diameter by 15.2 cm deep plastic pots seeded with 4 winter wheat seeds are convenient sizes for growth chamber or greenhouse studies. Any soil suitable for growth chamber studies can be used. One exemplary soil is Ritzville silt loam amended with 20% sand by weight. It is not necessary to surface-sterilize the seeds prior to planting.

The amount of bacteria per jointed goatgrass seed in the test pots is selected so as to optimize the selection of field-effective strains and minimize the selection of field-ineffective strains. We have found that a range of $10^8$ to $10^{10}$ colony forming units (CFU) of the test strain per jointed goatgrass test pot is applied to the soil surface. One convenient method is putting the test strain in a liquid such as distilled water or PMS and dripping the liquid on to the soil surface. Wheat seeds are grown in the presence of $10^8$ to $10^{10}$ CFU of the test strain per pot with 4 seeds to assess the effect of the bacteria on wheat. Separate jointed goatgrass and winter wheat controls are prepared identical to the test samples except without bacterial treatment.

The soil is wetted to provide good plant growth, and the pots incubated in the growth chamber. We have found that a 14-hour day at 18° C. and a 10-hour night at 13° C. is suitable. After about 3 to 4 weeks, the jointed goatgrass and wheat seedlings are pulled up and the roots washed with water until free of soil. The roots and shoots of the jointed goatgrass and wheat seedlings are excised and roots or shoots or both dried to remove water so that a comparison to control plants can be made. Drying at 60° C. for 48 hours is suitable.

Evaluation of Seedlings in the Growth Chamber Test

To evaluate the bacterial treatment, root or shoot dry weight of the jointed goatgrass plants is compared with the root or shoot dry weight of the control jointed goatgrass plants. Bacterial strains which cause the treated jointed goatgrass seedlings to have reduced root growth (reduced root dry weight when compared to the control) of at least 30% or which cause the treated jointed goatgrass seedlings to have reduced shoot growth (reduced shoot dry weight when compared to the control) of at least 30% are considered inhibitory to jointed goatgrass in this test.

To evaluate the bacterial treatment on wheat, root dry weight or shoot dry weight of the wheat plants are compared with the control wheat plants. For the purposes of this invention, a bacterial strain is denoted as one that does not deleteriously affect winter wheat when reduction in root growth (root dry weight) or shoot growth (shoot dry weight) of the bacterial treated wheat is less than 10% when compared to the control wheat seedlings.

Step 4: Screening the Bacterial Strains in the Field

Bacterial strains selected in the previous step are next tested in the field. Treatment and control plots are laid out. We have found that treatment plots consisting of 20 meters$^2$ are suitable. The control (non-treatment) should be within close proximity to the comparable treatment plot so that treatment and non-treatment plots have similar soil conditions.

For the field test, it is preferred that jointed goatgrass plants be grown in plots that are substantially free of other weeds so that variability due to the presence of other weeds is reduced. A convenient plot size is 2 to 3 meters wide by 9 meters long per treatment with a control plot within about 6 meters of the treatment plot. The plots are seeded to jointed goatgrass, about 50 to 75 seeds per meter$^2$. Individual bacterial strains to be tested are applied to the soil as a spray treatment. The treatment is applied just after planting to up to 4 weeks. The bacteria must be applied to moist soil to insure survival of the organisms. For the spray treatment, the test strain in a liquid such as distilled water or PMS is sprayed on to the soil to provide a concentration of about $10^8$ to $10^{12}$ CFU of the test strain per meter$^2$. Control plots are treated identical to the test plot except that no bacteria are applied. To have statistical significance, each organism treatment is replicated a minimum of three times.

Plots seeded to winter wheat (about 100 to 150 seeds per meter$^2$) are seeded beside or with the jointed goatgrass plots and the test organisms are sprayed on to the plots to provide a concentration of about $10^8$ to $10^{12}$ CFU of the test strain per meter$^2$. The treatment is applied to moist soil just after planting to up to 4 weeks after planting. The control plants receive identical treatment except that no bacteria are applied. To have statistical significance, each organism treatment is replicated a minimum of three times.

Evaluation of Seedlings in the Field Test

To assess the effect of the bacterial treatment in the inhibition of jointed goatgrass in the field, after adequate growth has occurred, e.g., about the 3- to 5-leaf stage, and at least one of the following is obtained: root dry weight, shoot dry weight, or stand (numbers of plant per meter$^2$). Bacterial strains which cause the treated jointed goatgrass plants to average a reduction in root growth (root dry weight), reduction in shoot growth (shoot dry weight), or reduction in stand of at least 20% when compared to control jointed goatgrass plants are considered inhibitory to jointed goatgrass in the field test. To assess the effect of the bacterial treatment on winter wheat, at least one of the following is obtained: root dry weight, shoot dry weight, or stand. Those bacterial strains which cause winter wheat to average less than 10% reduction in root growth (root dry weight), shoot growth (shoot dry weight) or stand compared to control wheat are defined as not deleteriously affecting the crop.

Application of Jointed Goatgrass-Inhibitory Bacteria For Control of Jointed Goatgrass in a Commercial Setting Methods useful to control jointed goatgrass in a commercial setting include: application of an inhibitory amount of bacteria to the soil surface or subsurface of the crop area or application of an inhibitory amount of bacteria with or to the small grain crop seed. The bacteria must be applied when the soil is moist to insure survival of the organisms. For spray applications, it is best to spray after a rain or shortly before and during periods of high rain probability. Soil application of the organisms should be done after seeding up to 4 weeks after seeding.

Individual strains of bacteria which inhibited jointed goatgrass in the growth chamber and field tests without deleteriously affecting wheat are cultured by standard methods for a time to grow sufficient bacteria to treat the field area, generally about 24–48 hours. The organisms are applied to the field in an amount sufficient to inhibit jointed goatgrass. Generally, this amount is about $10^8$ to $10^{12}$ CFU of inhibitory bacteria per meter$^2$.

EXAMPLES

The following examples are intended only to further illustrate the invention and are not intended to limit the scope of the invention which is defined by the claims.

EXAMPLE 1

Isolation of Strains

Winter wheat and jointed goatgrass plants were dug from the field and the roots washed free from adhering soil in flowing tapwater. The roots were excised and placed in a sterile dilution blank containing 95 ml of deionized water and glass beads. The mixture was vigorously shaken on a wrist-action shaker and serial dilutions prepared and spread plated on King's Medium B supplemented with 45 mg novobiocin, 45 mg penicillin G, and 75 mg cyclohexamide (Sands and Rovira, supra).

EXAMPLE 2

Initial Isolate Screening

Individual colonies obtained by the procedure outlined in Example 1 were screened in vitro as follows: Individual isolates were grown in PMS broth (Gasson, supra, KCl, 0.2 g; $NH_4H_2PO_4$, 1.00 g; $H_2O$, 100 ml; adjusted to pH 7.0, after autoclaving 20 ml sterile 2% $MgSO_4.7H_2O$, and 20 ml sterile 10% glucose added) at 20° C. until late logarithmic growth (0.9 O.D. at 600 nm on the spectrophotometer). The cultures were then centrifuged and filter sterilized to obtain a cell-free culture filtrate.

Plastic petri dishes received 2 ml of the culture filtrate. Control plates received 2 ml of fresh PMS. Then 18 ml of 0.9% molten bacto-agar (Difco) (50° C.) were added to each plate, and the contents mixed. When solidified, 10 dehusked jointed goatgrass seeds were planted on each plate, slanted, and allowed to grow at 15° C. Before root growth from the seedlings interfered with each other (5 days), the seedlings were pulled from the agar and root and shoot length were recorded. The organisms which showed at least a 50% reduction in root growth when compared to the control were denoted as inhibitory to jointed goatgrass and were tested against winter wheat seedling growth. Test tubes received 1 ml the cell-free culture filtrate. Control tubes received 1 ml of fresh PMS. Then 9 ml of 0.9% molten bacto-agar (50° C.) were added to each tube, the contents mixed, and the tubes slanted. When solidified, a pregerminated wheat seed was planted mid-slope on each slant and allowed to grow at 15° C. Before root growth reached the bottom of the tube (3 days), the seedlings were pulled from the growth tubes and root and shoot length recorded. In order for the bacterial strain to be considered not to be deleterious to winter wheat, the wheat seedlings treated with the bacteria must have averaged less than 25% reduced root growth when compared to the control plants.

The test results for nine strains are given in Table 1. The data are an average of 30 seedlings per treatment. Cultures retained for further studies were individually streaked and selected and restreaked until the strain was pure and stable and stored in sterile aqueous glycerol at −10° C.

TABLE 1

| | Jointed Goatgrass | | Winter Wheat | |
|---|---|---|---|---|
| Isolate | Root Length (mm) | Reduction In Root Growth Compared to Control (%) | Root Length (mm) | Reduction In Root Growth Compared to Control (%) |
| Set 1: | | | | |
| Control | 16.8 | — | 65.0 | — |
| 3361 | 10.8 | 35 | 54.6 | 16 |
| 3725 | 6.4 | 62 | 71.5 | None |
| 3636 | 5.9 | 65 | 50.7 | 22 |
| D6 | 5.3 | 68 | 67.1 | None |
| Set 2: | | | | |
| Control | 22.7 | — | 75.4 | — |
| 47-3 | 2.5 | 89 | 58.8 | 22 |
| 47-7 | 3.4 | 85 | 70.1 | 7 |
| 56-4 | 7.3 | 68 | 71.6 | 5 |
| 71-10 | 5.3 | 77 | 62.6 | 17 |
| 47-5 | 2.9 | 87 | 69.8 | 7 |

EXAMPLE 3

Screening of Bacterial Strains in the Growth Chamber

Strains were screened in the growth chamber to determine the effect of the isolates on test plants grown in soil. Six dehusked jointed goatgrass seeds were seeded into 6.4 cm diameter by 7.6 cm deep plastic pots filled with Ritzville silt loam plus 20% fine sand (w/w), and four winter wheat seeds were seeded into 7.6 cm diameter by 15.2 cm deep plastic pots filled with Ritzville silt loam with 20% fine sand (w/w). Approximately $10^8$ CFU of each strain tested were dripped on the soil surface on the seeded area in the jointed goatgrass and winter wheat seeded pots. Controls received the fresh noninoculated medium. Four replicates of each treatment were included. The soil was wetted to −⅓ bar water potential, and the pots incubated in the growth chamber with a 14-hour day at 18° C. and a 10-hour night at 13° C.

Seedling emergence was determined. After 2 weeks the seedlings were pulled up and the roots washed with water until free of soil. The roots and shoots were excised, dried at 60° C. for 48 hours, and dry shoot and root weight recorded. In order for the bacterial strain to be considered to be inhibitory to jointed goatgrass without deleteriously affecting wheat, the jointed goatgrass seedlings treated with the bacteria must have averaged at least 30% reduced root growth (dry root weight) when compared to control jointed goatgrass seedlings, and the winter wheat seedlings treated with the bacteria must have averaged less than 10% reduced root growth (dry root weight) when compared to control wheat seedlings. The test results for the strains are given in Table 2.

TABLE 2

| | Jointed Goatgrass | | Winter Wheat | |
|---|---|---|---|---|
| Isolate | Root wt/pot (mg) | Reduction In Root Growth Compared to Control (%) | Root wt/ plant (mg) | Reduction In Root Growth Compared to Control (%) |
| Set 1: | | | | |
| Control | 89 | — | 30 | — |
| 3361 | 40 | 55 | 46 | None |
| 3725 | 46 | 48 | 35 | None |
| 3636 | 42 | 53 | 43 | None |
| D6 | 44 | 51 | 34 | None |
| Set 2: | | | | |
| Control | 94 | — | 45 | — |
| 47-3 | 33 | 65 | 54 | None |
| 47-7 | 50 | 47 | 44 | 2 |
| 56-4 | 60 | 36 | 42 | 7 |

TABLE 2-continued

| Isolate | Jointed Goatgrass | | Winter Wheat | |
|---|---|---|---|---|
| | Root wt/pot (mg) | Reduction In Root Growth Compared to Control (%) | Root wt/ plant (mg) | Reduction In Root Growth Compared to Control (%) |
| 71-10 | 51 | 46 | 43 | 4 |
| 47-5 | 65 | 31 | 48 | None |

EXAMPLE 4

Field Screening of Bacteria to Inhibit Jointed Goatgrass Growth

Strains that passed the growth chamber test were field tested in Lind, Wash. during the 1988-1989 growing season as follows: PMS broth was inoculated with glycerol-preserved-strains and incubated at 20° C. for 2 days. Agar plates of PMS medium were prepared and each inoculated with 1 ml of the PMS broth culture medium containing the individual strains. One ml of inoculum was spread on the plate with a sterile glass rod. A sufficient number of plates were inoculated to provide organisms to treat the field plots at $10^8$ CFU of the test strain/m$^2$. The plates were incubated at 15° C. for 3 days to obtain maximum growth. The plates were flooded with sterile deionized water, and the organisms mixed in the water by agitation of the surface of the plate with a glass rod. The plate washings for each strain were pooled. The suspension was diluted with sterile deionized water to an optical density of 0.9 (determined on a spectrophotometer at 600 nm). The amount of this solution necessary to treat the plot area was added to a $CO_2$ backpack sprayer with water as a carrier at 20 gallons of solution per acre.

Plots were 20 meters$^2$ with 1 meter between plots arranged in a randomized complete block design. Each treatment was replicated four times (sprayed with the test strain or a water-check). Before the organisms were added, the plots were hand seeded by broadcasting jointed goatgrass seed onto the soil surface at 50 to 75 seeds/meter$^2$. The jointed goatgrass seed was incorporated about 3 cm deep with a harrow. Then, plots were seeded to winter wheat at about 100 to 150 seeds/meter$^2$ in rows 0.4 meters apart. The organisms or water treatments were sprayed on to moist soil after planting.

In early April, jointed goatgrass and winter wheat plants in three 0.25 meter$^2$ quadrats were counted in each plot to obtain plot stands. In order for the bacterial strain to be considered inhibitory to jointed goatgrass in the field test, the jointed goatgrass plants treated with the bacteria must average at least 20% reduced stand when compared to the control jointed goatgrass plants. Table 3 shows data from the field test. In order for the bacterial strain to be denoted as not deleterious to wheat, the reduction in stand of treated wheat plants must be less than 10% compared to control wheat plants. Winter wheat treated with the strains showed no reduction in stand compared to control winter wheat.

TABLE 3

| Isolate | Jointed Goatgrass | |
|---|---|---|
| | Plants/m$^2$ | Reduction In Stand (%) |
| Control | 34 | |
| 3361 | 30 | 12 |
| 3725 | 37 | None |

TABLE 3-continued

| Isolate | Jointed Goatgrass | |
|---|---|---|
| | Plants/m$^2$ | Reduction In Stand (%) |
| D6 | 41 | None |
| 47-3 | 31 | 9 |
| 47-7 | 13 | 62 |
| 56-4 | 33 | 3 |
| 71-10 | 36 | None |
| 47-5 | 26 | 24 |

Of 2500 isolates tested, two isolates (47-7 and 47-5) passed the screen test. Isolates 47-7, 47-5, and 3361 have been identified as Pseudomonas species.

Statement of Deposit. Pure cultures of isolates 47-7 and 47-5 have been deposited at 218 Johnson Hall, Washington State University, Pullman, Wash.

Pure cultures of these isolates have also been deposited under the provisions of the Budapest Treaty in the Agricultural Research Culture Collection (NRRL) in Peoria, Il, and have been assigned Accession Nos. NRRL B-18776, and NRRL B-18777, respectively.

It is understood that the foregoing detailed description is given merely by way of illustration and that modification and variations may be made therein without departing from the spirit and scope of the invention.

Having thus described our invention, we claim:

1. A method for screening bacteria to select strains which will inhibit jointed goatgrass growth in field grown small grain crops without deleteriously affecting the small grain crop, which comprises:
   (a) isolating a strain of bacteria from the rhizoplane, rhizosphere, or both rhizoplane and rhizosphere of jointed goatgrass or a small grain crop grown in the field;
   (b) screening said strain isolated in step (a) for inhibition of jointed goatgrass growth without deleteriously affecting the small grain crop in vitro as follows:
      (1) growing jointed goatgrass in vitro in the presence of a cell culture of said strain isolated in step (a), a substantially cell-free culture supernatant obtained from said strain isolated in step (a) or a cell-free culture filtrate obtained from said strain isolated in step (a);
      (2) growing jointed goatgrass as in step (b)(1) without the addition of said cell culture, said culture supernatant, or said culture filtrate;
      (3) selecting a strain which caused jointed goatgrass of step (b)(1) to average at least a 50% reduction in root growth or at least a 20% reduction in germination compared to jointed goatgrass grown in step (b)(2);
      (4) growing the small grain crop of the variety to be protected in vitro in the presence of a cell culture of said strain selected in step (b)(3), a substantially cell-free culture supernatant obtained from said strain selected in step (b)(3), or a cell-free culture filtrate of said strain selected in step (b)(3);
      (5) growing said small grain crop of the variety to be protected as in step (b)(4) without the addition of said cell culture, said culture supernatant, or said culture filtrate; and
      (6) selecting a strain which caused said small grain crop of step (b)(4) to average less than 25% reduction in root growth compared to said small grain crop grown in step (b)(5);

(c) screening said strain selected in step (b)(6) for inhibition of jointed goatgrass without deleteriously affecting the small grain crop in a growth chamber as follows:
  (1) separately growing jointed goatgrass and the small grain crop of the variety to be protected in the growth chamber in the presence of said strain selected in step (b)(6) in a concentration of about $10^8$ to $10^{10}$ CFU of said strain per 6 to 10 jointed goatgrass seeds and in a concentration of about $10^8$ to $10^{10}$ CFU of said strain per 4 small grain crop seeds;
  (2) growing jointed goatgrass and said small grain crop as in step (c)(1) without the addition of said strain; and
  (3) selecting a strain which caused jointed goatgrass of step (c)(1) to average at least a 30% reduction in root growth or at least a 30% reduction in shoot growth compared to jointed goatgrass grown in step (c)(2) and which caused said small grain crop grown in step (c)(1) to average less than 10% reduction in root growth or shoot growth compared to said small grain crop grown in step (c)(2);

(d) screening said strain selected in step (c)(3) for inhibition of jointed goatgrass without deleteriously affecting the small grain crop in a field as follows:
  (1) growing jointed goatgrass and the small grain crop of the variety to be protected in the field in the presence of said strain selected in step (c)(3) in a concentration of about $10^8$ to $10^{12}$ CFU of said strain per meter$^2$ of said jointed goatgrass and said small grain crop;
  (2) growing jointed goatgrass and said small grain crop as in step (d)(1) without the addition of said strain; and
  (3) selecting a strain which caused jointed goatgrass of step (d)(1) to average at least a 20% reduction in stand, root growth, or shoot growth compared to jointed goatgrass grown in step (d)(2) and which caused said small grain crop grown in step (d)(1) to average less than 10% reduction in stand, root growth, or shoot growth compared to said small grain crop grown in step (d)(2).

2. The method of claim 1, further comprising:
(e) applying said strain of bacteria selected in step (d)(3) to field grown small grain crops of the variety to be protected in an amount sufficient to inhibit the growth of jointed goatgrass in said crop.

3. The method of claim 2 wherein said strain is applied in a concentration of about $10^8$ to $10^{12}$ CFU per meter$^2$.

4. The method of claim 3 wherein said strain is applied as a spray treatment comprising said strain in a liquid carrier.

5. The method of claim 2 wherein said strain is applied as a small grain crop seed treatment.

6. The method of claim 2 wherein said small grain crop is winter wheat.

7. A method for controlling jointed goatgrass growth in a field of a small grain crop without deleteriously affecting the small grain crop, comprising applying to the field of the variety of small grain crops to be protected a strain of bacterium indigenous to the rhizoplane and/or the rhizosphere of jointed goatgrass or the small grain crop in an amount sufficient to inhibit the growth of the jointed goatgrass, wherein the bacterium is characterized by the property of causing jointed goatgrass grown in the presence of the small grain crop to average at least a 20% reduction in stand, root growth measured on a dry weight basis, or shoot growth measured on a dry weight basis when the bacterium is applied at a concentration of about $10^8$ to $10^{12}$ CFU of bacterium per meter$^2$ as compared to jointed goatgrass grown in the absence of said bacterium, and wherein the bacterium is further characterized by causing the small grain crop to average less than a 10% reduction in the stand, root growth measured on a dry weight basis, or shoot growth measured on a dry weight basis when the bacterium is applied at a concentration of about $10^8$ to $10^{12}$ CFU of bacterium per meter$^2$ as compared to the crop grown in the absence of the bacterium.

8. A method as described in claim 7 wherein said property is determined when said jointed goatgrass and said crop are grown together.

9. A method as described in claim 7 wherein said bacterium is Pseudomonas sp. NRRL B-18776.

10. A method as described in claim 7 wherein said bacterium is Pseudomonas sp. NRRL B-18777.

11. An agricultural composition for controlling jointed goatgrass growth in a field of a small grain crop without deleteriously affecting the small grain crop, said composition comprising a carrier and an amount sufficient to inhibit the growth of the jointed goatgrass of a strain of bacterium indigenous to the rhizoplane and/or the rhizosphere of jointed goatgrass or the small grain crop, wherein the bacterium is characterized by the property of causing jointed goatgrass grown in the presence of the small grain crop to average at least a 20% reduction in stand, root growth measured on a dry weight basis, or shoot growth measured on a dry weight basis when the bacterium is applied at a concentration of about $10^8$ to $10^{12}$ CFU of bacterium per meter$^2$ as compared to jointed goatgrass grown in the absence of said bacterium, and wherein the bacterium is further characterized by causing the small grain crop to average less than a 10% reduction in the stand, root growth measured on a dry weight basis, or shoot growth measured on a dry weight basis when the bacterium is applied at a concentration of about $10^8$ to $10^{12}$ CFU of bacterium per meter$^2$ as compared to the crop grown in the absence of the bacterium.

12. A composition as described in claim 11 wherein said property is determined when said jointed goatgrass and said crop are grown together.

13. A composition as described in claim 11 wherein said bacterium is Pseudomonas sp. NRRL B-18776.

14. A composition as described in claim 11 wherein said bacterium is Pseudomonas sp. NRRL B-18777.

* * * * *